US00PP22996P2

(12) United States Plant Patent
Kerley et al.

(10) Patent No.: US PP22,996 P2
(45) Date of Patent: Aug. 28, 2012

(54) ***VIOLA* PLANT NAMED 'KERVIOCHEEKY'**

(50) Latin Name: *Viola×wittrockiana*
Varietal Denomination: KERVIOCHEEKY

(76) Inventors: David Kerley, Cambridge (GB); Priscilla Grace Kerley, Cambridge (GB); Timothy Edward Kerley, Cambridge (GB)

( * ) Notice: Subject to any disclaimer, the term of this patent is extended or adjusted under 35 U.S.C. 154(b) by 0 days.

(21) Appl. No.: 13/065,158

(22) Filed: Mar. 14, 2011

(51) Int. Cl.
*A01H 5/00* (2006.01)

(52) U.S. Cl. ..... Plt./323

(58) Field of Classification Search ..... Plt./323
See application file for complete search history.

*Primary Examiner* — Annette Para
(74) *Attorney, Agent, or Firm* — Cassandra Bright

(57) ABSTRACT

A new and distinct *Viola×wittrockiana* cultivar named 'KERVIOCHEEKY' is disclosed, characterized by a unique combination of a large, round "pansy" type flower, found on a trailing plant. Flower color is a bright Yellow with a Brown to Greyed-Purple blotch, flowers have a wavy petal margin. Plants have a compact, trailing plant habit. The new variety is a *Viola×wittrockiana*, suitable for outdoor landscape and container use.

2 Drawing Sheets

Figure 1:
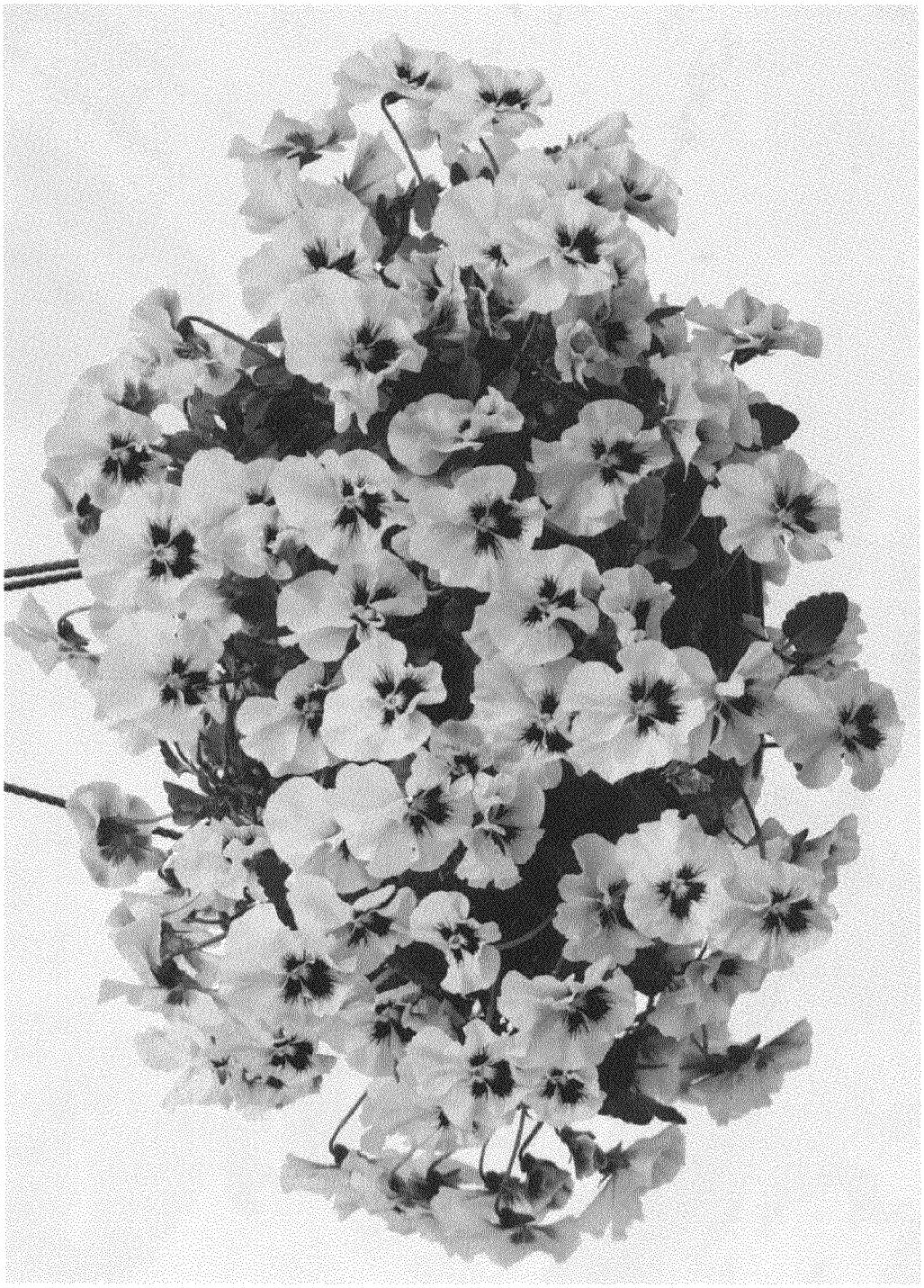

Latin name of the genus and species: *Viola×wittrockiana.*
Variety denomination: 'KERVIOCHEEKY'.

BACKGROUND OF THE INVENTION

The new cultivar is the product of a planned breeding program under the direction of the inventors, David Kerley, Priscilla Kerley and Timothy Kerley, all citizens of the United Kingdom. The objective of the breeding program was to produce new trailing *Viola×wittrockiana* cultivars for commercial ornamental purposes. The new cultivar resulted from the crossing of two unpatented proprietary seedlings. The seed parent was referred to as '05-40-1' and the pollen parent was referred to as '05-5-2'. The cross resulting in 'KERVIOCHEEKY' was performed during May of 2005. The selection of the new variety 'Kerviocheeky' was made in April 2006, by the inventors at a research greenhouse located in Cambridge, UK.

Asexual reproduction of the new cultivar 'KERVIOCHEEKY' by vegetative cuttings was first performed at the same research greenhouse in Cambridge, UK in July of 2006, and has shown that the unique features of this cultivar are stable and reproduced true to type in successive generations.

SUMMARY OF THE INVENTION

The cultivar 'KERVIOCHEEKY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'KERVIOCHEEKY' These characteristics in combination distinguish 'KERVIOCHEEKY' as a new and distinct *Viola* cultivar:

1. Unique round "pansy" flower, on a trailing *Viola* plant, rather than the elongated flower form more commonly found on spreading or trailing types which are usually *Viola×williamsii.*
2. Large uniquely rounded flower shape.
3. Spreading, trailing plant habit.

4. Exceptionally compact habit when grown in a small container.
5. Bright yellow, with dark blotch flower color.

PARENT COMPARISON

Plants of the new cultivar 'KERVIOCHEEKY' are similar to plants of the seed parent variety, in most horticultural characteristics. However, plants of the new cultivar produce smaller flowers, of a different color. Additionally, the new variety produces a plant with a more trailing habit than the seed parent, and flowers that are less undulating.

Plants of the new cultivar 'KERVIOCHEEKY' are similar to plants of the pollen parent variety, in most horticultural characteristics. However, plants of the new cultivar produce larger flowers, with a blotch, whereas the parent variety has no blotch. Additionally, the new variety produces flowers that are more undulating than flowers of the pollen parent.

COMMERCIAL COMPARISON

Plants of the new cultivar 'KERVIOCHEEKY' are similar to plants of the commercial variety known as *Viola* 'Sunvioki' U.S. Plant Pat. No. 16,138, in some horticultural characteristics. However, plants of the new cultivar 'KERVIOCHEEKY' produce larger flowers, with a rounded flower shape and a blotch not found in 'Sunvioki'. Additionally, 'KERVIOCHEEKY' produces thicker plant and flower stems, and larger leaves than 'Sunvioki'.

BRIEF DESCRIPTION OF THE PHOTOGRAPHS

The accompanying photograph in FIG. 1 illustrates in full color typical plants of 'KERVIOCHEEKY' grown in a poly house in Cambridge, UK. Plants are approximately 35 weeks old shown in a 20 cm basket, 3 rooted cuttings were planted per pot.

Figure 2:
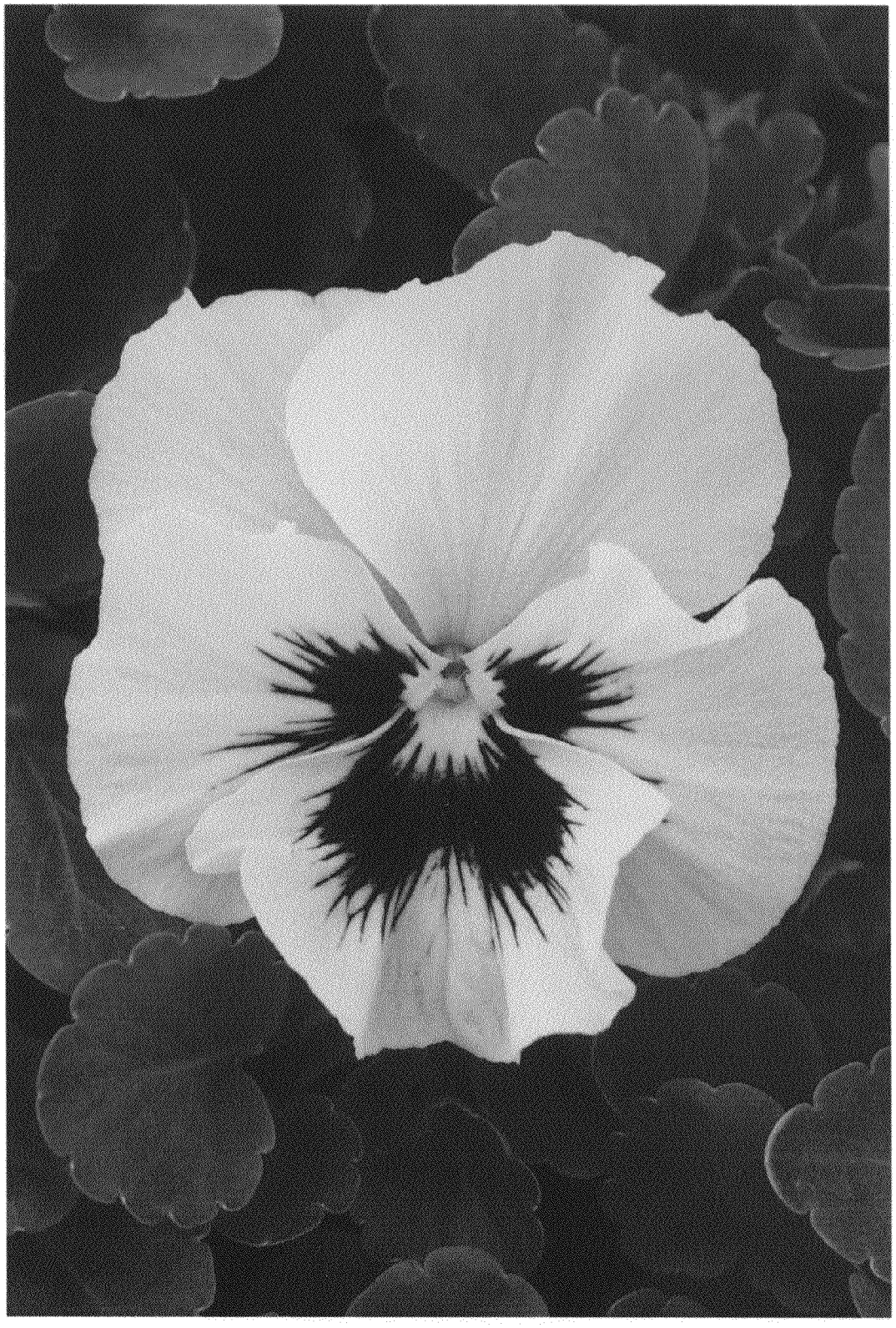

FIG. 2 illustrates a close up of a typical flower of 'KERVOICHEEKY'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 1995 except where general terms of ordinary dictionary significance are used. The following observations and measurements describe 'KERVIOCHEEKY' plants grown in an unheated poly house in Cambridge, UK. The growing temperature ranged from approximately −5 to 12° C. at night to −2 to 18° C. during the day. 3 rooted cuttings were planted in a 20 cm basket. No chemical or photoperiodic treatments were given. Measurements and numerical values represent averages of typical flowering types.

Botanical classification: *Viola×wittrockiana* 'KERVIOCHEEKY.'

Age of the plant described: Approximately 37 weeks, in a 20 cm basket.

PROPAGATION

Time to rooting: About 15 to 20 days at approximately 20° C.

Root description: Fine, fibrous.

PLANT

Growth habit: Spreading, trailing.

Height: Approximately 20 cm.

Plant spread: Approximately 60 cm.

Branching characteristics: Free branching.

Diameter of lateral branches: Approximately 0.5 cm.

Length of lateral branches: Approximately 19 cm.

Texture of lateral branches: Glabrous.

Internode length: Approximately 4 cm.

Strength of stem: Strong.

Color of lateral branches: Near RHS Yellow-Green 144A.

Quantity of lateral and sub lateral branches: Approximately 65.

FOLIAGE

Leaf:

*Arrangement*.—Alternate.

*Average length*.—Approximately 5.4 cm.

*Average width*.—Approximately 2.2 cm.

*Shape of blade*.—Obovate.

*Apex*.—Rounded.

*Base*.—Cordate.

*Attachment*.—Petioled.

*Margin*.—Crenulate.

*Texture of top surface*.—Glabrous.

*Texture of bottom surface*.—Glabrous.

*Color*.—Developing foliage upper side: Near R.H.S. Green 137A. Developing foliage under side: Near R.H.S. Green 137C. Mature foliage upper side: Near R.H.S. Yellow-Green 147A. Mature foliage under side: Near R.H.S. Green 137B.

*Venation*.—Type: Pinnate. Venation color upper side: Near R.H.S. Green 139D. Venation color under side: Near R.H.S. Green 139D.

Petiole:

*Length*.—Approximately 2.8 cm.

*Diameter*.—0.2 cm.

*Color*.—Near RHS Yellow-Green 144A, upper petiole, lower petiole near 144B.

FLOWER

Bloom period: Naturally blooming March to November under United Kingdom outdoor conditions.

Inflorescence:

*Form*.—Single, axillary flowers, comprised of 5 petals total; 2 upper, 2 lateral and 1 lower in a single whorl. Petals undulating.

Flower longevity on plant: About 5 days.

Persistent or self-cleaning: Self-Cleaning.

Fragance: Slightly fragrant.

Flowers per plant: Approximately 168.

Flower bud:

*Bud color*.—Near RHS Green-Yellow 1D heavily flushed Purple-Violet 81B or Purple 79D, varying flush coloration.

*Bud length*.—Approximately 2.0 cm.

*Bud diameter*.—Approximately 1.1 cm.

Individual flower:

*Flower size*.—Length: Approximately 63 cm. Width: Approximately 5.7 cm.

*Petal texture*.—All petals, glabrous, velvety with matte appearance.

Petals:

*Upper petals*.—Shape: Orbicular. Length: Approximately 3.2 cm. Width: Approximately 4.2 cm. Margin: Entire. Apex: Rounded. Color: When opening, upper surface: Near RHS Yellow 7A overlaid with Grey-Brown 199C towards tip; vein Green 138B. When opening, lower surface: Near RHS 7A to 7B, veins Violet 83A, prominent towards base; bleeding between veins greyed Purple 77B at base; Partly overlaid with Greyed-Green 197C towards tip. Fully opened, upper surface: Deeper than Yellow 9A; slight venation coloration near Greyed-Green 195B, more intense at base. Fully opened, lower surface: Near RHS Yellow 9B: prominent veins greyed 77A through C; bleeding between veins at petal base greyed Purple 78C.

*Lateral petals*.—Shape: Reniform. Length: Approximately 3.2 cm. Width: Approximately 3.6 cm. Margin: Entire. Apex: Rounded. Color: When opening, upper surface: Near RHS Yellow 7A overlaid with varying amounts of Greyed-Brown 199C; blotch at base Brown 200A. When opening, lower surface: Near RHS Yellow 7B overlaid with Greyed-Green 197D in places; vein towards base Violet 86A-C; reverse of blotch Greyed-Purple 183A. Fully opened, upper surface: A color Between 9A and 13A; blotch at base closest to Greyed-Purple 187A. Fully opened, lower surface: Near RHS Yellow 9B; veins at base Violet 88A-B; overlaid with Greyed-Orange 176C towards base.

*Lower petal*.—Shape: Very broad obocordate to orbicular. Length: Approximately 3.3 cm. Width: Approximately 4.1 cm. Margin: Entire. Apex: Rounded. Color: When opening, upper surface: Deeper than Yellow 9A; blotch Brown 200A; eye Yellow 14B. When opening, lower surface: Near RHS Yellow 9B overlaid with Yellow-Green 145C towards base at reverse of blotch. Fully opened, upper surface: Near RHS Yellow 14A nearest; blotch Greyed-Purple 187A; eye Yellow 17B. Fully opened, lower surface: Near RHS Yellow 12A overlaid with Yellow-Green 144D at base; vein Greyed-Green 191C towards base.

Additional flower data:

*Spur on flower petal*.—Length: Approximately 0.4 cm. Width: Approximately 0.1 cm. Depth: Approximately 0.3 cm. Color: Near RHS Blue-Green 122B, but, more grey.

*Eye dimensions*.—Length: Approximately 0.5 cm. Width: Approximately 0.4 cm.

Sepals:

*Quantity*.—5.
*Arrangement*.—Whorled.
*Length*.—Approximately 1.6 to 2.2 cm.
*Width*.—Approximately 0.6 cm.
*Color*.—Near RHS Green 137B.
*Shape*.—Elliptic.
*Apex*.—Acute.
*Base*.—Obtuse.
*Texture*.—Glabrous.

Peduncle:

*Peduncle length*.—Approximately 12.5 cm.
*Peduncle diameter*.—Approximately 0.2 cm.
*Aspect*.—Upright with outward curve.
*Color*.—Near RHS Yellow-Green 144A.
*Texture*.—Glabrous.

REPRODUCTIVE ORGANS

*Stamen quantity*.—Approximately 5.
*Filament length*.—Approximately 0.1 cm.
*Anther length*.—Approximately 0.4 cm.
*Anther color*.—Near RHS Yellow-White 158D.
*Pollen color*.—Near RHS Yellow 10C.
*Pollen amount*.—Scant to moderate.
*Style length*.—Approximately 0.2 cm.
*Style length*.—Approximately 0.2 cm.
*Stigma shape*.—Bulbous with concave depression on uppermost portion.
*Ovary color*.—Near RHS Green 138B.
*Stigma color*.—Near RHS Yellow-Green 151B.

OTHER CHARACTERISTICS

Disease resistance: Neither resistance nor susceptibility to diseases or pests has been observed in this variety.

Temperature tolerance: Tolerates high temperature to at least 35° C. Tolerates low temperatures to −10° C.

Fruit/seed production: Fruit and seed production not observed.

What is claimed is:

1. A new and distinct cultivar of *Viola* plant named 'KERVIOCHEEKY' as herein illustrated and described.

* * * * *